United States Patent [19]

Martens et al.

[11] Patent Number: 5,482,684
[45] Date of Patent: Jan. 9, 1996

[54] VESSEL USEFUL FOR MONITORING PLASMA STERILIZING PROCESSES

[75] Inventors: Phillip A. Martens, Fremont, Calif.; Ross A. Caputo, Long Grove, Ill.

[73] Assignee: Abtox, Inc., Mundelein, Ill.

[21] Appl. No.: 237,268

[22] Filed: May 3, 1994

[51] Int. Cl.$^6$ ............... G01D 11/26; A61L 2/00; C12Q 1/18; C12M 1/34
[52] U.S. Cl. ............... 422/119; 422/21; 422/23; 422/28; 422/121; 422/906; 435/31; 435/32; 435/287.4
[58] Field of Search ............... 422/21, 23, 28, 422/119, 121, 906; 435/31, 33, 291, 296; 315/111.21

[56] References Cited

U.S. PATENT DOCUMENTS

| | | | |
|---|---|---|---|
| 3,851,436 | 12/1974 | Fraser et al. | 53/434 |
| 3,948,601 | 4/1976 | Fraser et al. | 422/23 |
| 4,314,344 | 2/1982 | Johns et al. | 364/500 |
| 4,643,876 | 2/1987 | Jacobs et al. | 422/23 |
| 4,671,936 | 6/1987 | Barron | 422/55 |
| 4,756,882 | 7/1988 | Jacobs et al. | 422/23 |
| 4,885,253 | 12/1989 | Kralovic | 435/296 |
| 4,914,034 | 4/1990 | Welsh et al. | 435/296 |
| 5,115,166 | 5/1992 | Campbell et al. | 315/111.21 |
| 5,184,046 | 2/1993 | Campbell | 315/111.21 |
| 5,200,146 | 4/1993 | Goodman | 422/23 |
| 5,244,629 | 9/1993 | Caputo et al. | 422/22 |
| 5,325,020 | 6/1994 | Campbell et al. | 315/111.21 |

OTHER PUBLICATIONS

"Standard for BIER/Steam Vessels," Association for the Advancement of Medical Instrumentation, pp. 17–29, Mar. 27, 1981.
"Standard for BIER/EO Gas Vessels" Association for the Advancement of Medical Instrumentation, pp. 1–29 [minus pp. 2, 4, 6, 8, 14 & 18 which were blank], Mar. 3, 1982.
Joslyn Valve Corp.'s product literature on Biological Indicator Evaluator Resistometer (BIER), undated.
U.S. Pharmacopeia XXII, Official Monograph, pp. 1625–1626.

Primary Examiner—Robert J. Warden
Assistant Examiner—Christopher Y. Kim
Attorney, Agent, or Firm—Majestic, Parsons, Siebert & Hsue

[57] ABSTRACT

A system for testing sterilization processes is provided by a vessel having a chamber, a plasma generator adapted to generate a plasma upstream of the chamber, a monitor associated with the chamber, and a biological or chemical indicator disposable within the chamber. The plasma generator generates upstream plasma that contains a plurality of atomic and/or molecular species, and the monitor is capable of determining a concentration of selected species in the plasma when flowing through the chamber.

20 Claims, 2 Drawing Sheets

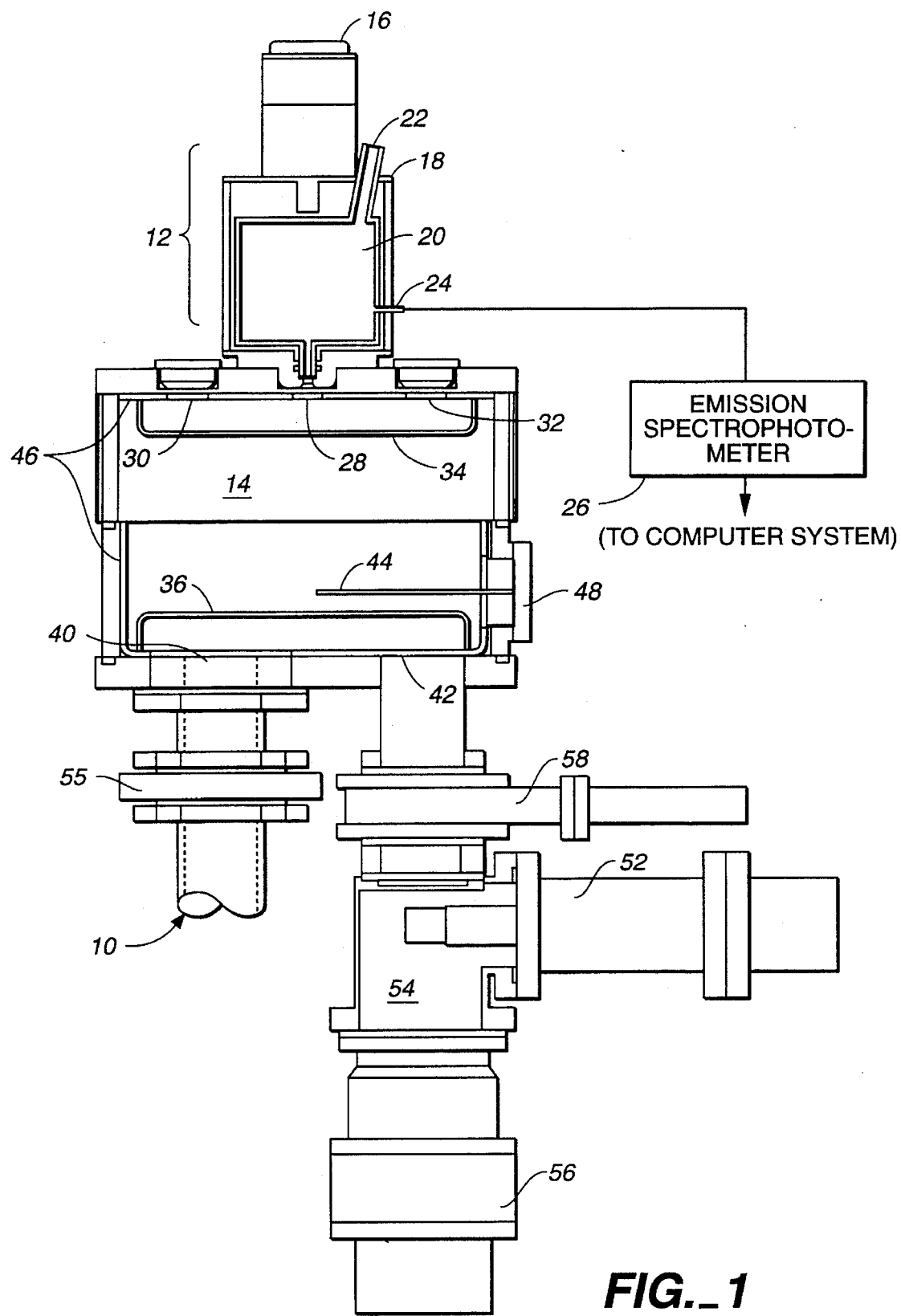
FIG._1

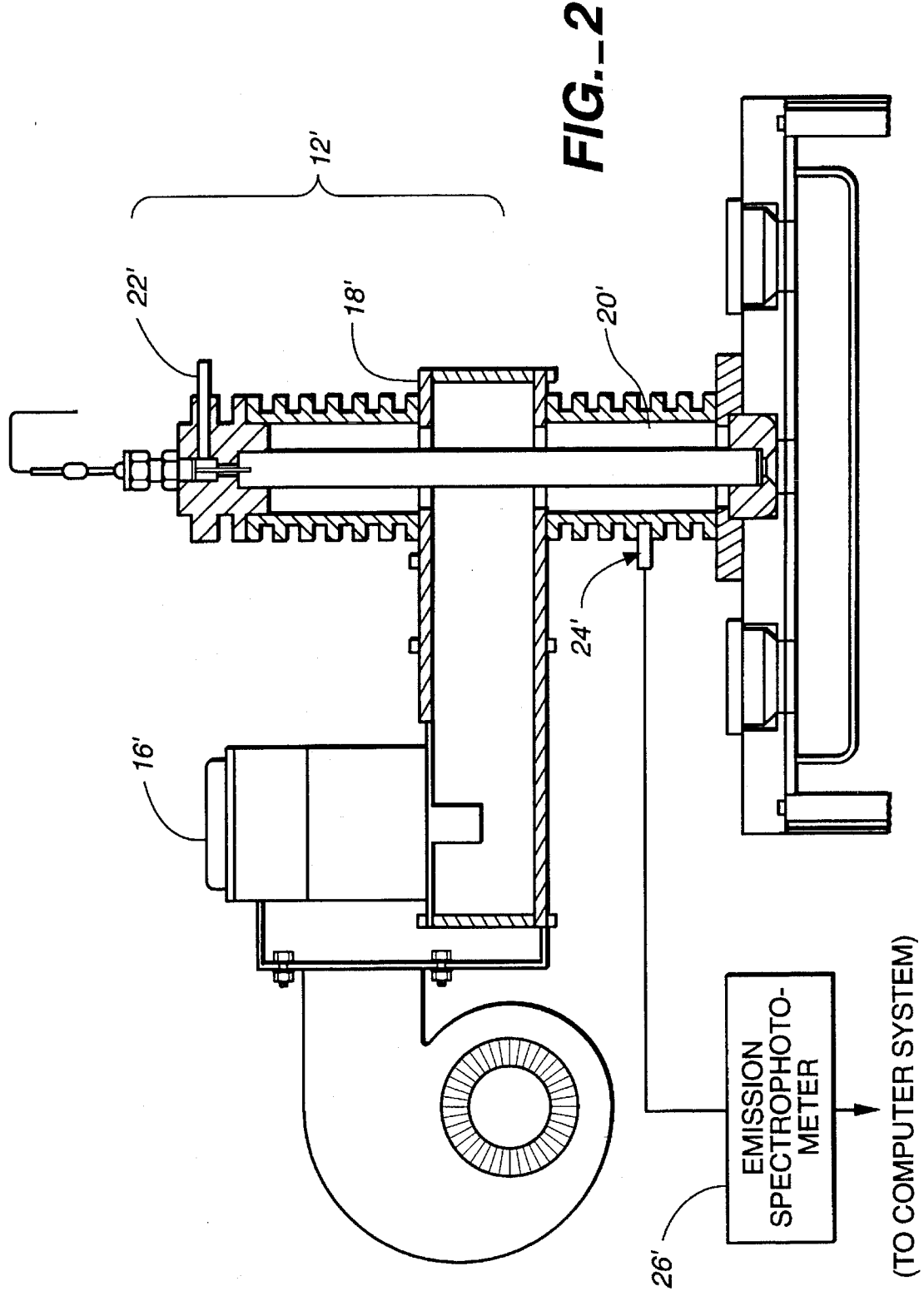
FIG._2

VESSEL USEFUL FOR MONITORING PLASMA STERILIZING PROCESSES

FIELD OF THE INVENTION

This invention relates to a plasma sterilization process, and particularly relates to a vessel to test the performance of indicators (biological and chemical) exposed to a plasma sterilization process and that may optionally also include a treatment cycle with a gaseous or vaporized antimicrobial agent.

BACKGROUND OF THE INVENTION

Steam and gas sterilization methods using either steam or ethylene oxide (or other disinfecting gases) are used for sterilizing a wide range of medical products from pharmaceutical preparations to surgical instruments.

A sterilizing method must effectively kill all organisms, including bacterial spores, without damage to the article or goods being sterilized. However, many sterilizing gases which meet these criteria, such as ethylene oxide, have been recognized to expose workers and the environment to safety hazards. Legislation is severely restricting the amount of hazardous gases such as ethylene oxide (a carcinogen) in the working environment, or the use of any system or method which produces toxic residues or exhaust products. This is presenting a major crisis in hospitals and other areas of the health industry. Although steam avoids this hazard, it is not useful for items and packaging materials that are unable to withstand high temperatures.

Sterilizing methods can be monitored by components such as biological indicators (BIs) and chemical indicators, both of which are used to monitor different performance aspects of sterilizing methods.

The *U.S. Pharmacopeia XXII, Official Monograph*, pp. 1625–1626 defines a biological indicator as "a characterized preparation of specific microorganisms resistant to a particular sterilization process. It is used to assist in the qualification of the physical operation of sterilization apparatus in the development and establishment of a validated sterilization process for a particular article, and the sterilization of equipment, materials, and packaging components for aseptic processing. It may also be used to monitor a sterilization cycle, once established, and periodically in the program to revalidate previously established and documented sterilization cycles. It is in one of two main forms, each of which incorporates a viable culture of a known species of microorganism. In one the spores are added to a carrier (disk or strip of filter paper, glass, or plastic) and packaged so as to maintain the integrity of the inoculated carrier but, when used appropriately in the individual immediate package, so as to allow the sterilizing agent to exert its effect. In the other, the spores are added to representative units of the lot to be sterilized (inoculated product) or to similar units (inoculated similar product)."

The need to develop sterilization methods avoiding the use of a hazardous gas such as ethylene oxide and the desirability of sterilization processes suitable for packages containing cellulose or those whose integrity can be destroyed at higher pressures or temperatures has lead to other sterilization processes, and other biological indicators. For example, *Bacillus stearothermophilus*, which is recognized as an organism useful in biological indicators for steam sterilizations, has been found to have a curvilinear response curve to oxidizing gas sterilization processes. This is disadvantageous because inactivation of an indicator organism must occur in a predictable manner.

Chemical indicators are generally used to monitor whether or not an article has been exposed to sterilizing conditions. A chemical indicator response is not necessarily an indication of sterility because it only indicates that the chemical indicator and any accompanying articles has been processed in a sterilizer.

Chemical indicators have been developed and are used with both of the prevalent sterilization processes: steam and ethylene oxide. For example, U.S. Pat. No. 4,914,034, issued Apr. 3, 1990, inventors Welsh and Dyke, describes disposable test packs for monitoring steam and ethylene oxide sterilization cycles, which include a chemical process indicator strip. U.S. Pat. No. 4,671,936, issued Jun. 9, 1987, inventor Barron, describes a cation exchange resin for monitoring alkylene oxide (including ethylene oxide) cycles.

Plasma gas sterilizer systems are described in U.S. Pat. Nos. 3,851,436 and 3,948,601 and comprise separate plasma RF generation chambers and sterilizing chambers. A gas plasma is produced in the plasma generating chamber with argon, helium, nitrogen, oxygen, or xenon, which is passed into a separate sterilization vacuum chamber containing the articles to be sterilized.

Numerous other gas plasma sterilizers using a wide variety of gases have been described in the literature. A few have been commercially produced. For example, one system is described in U.S. Pat. No. 4,643,876. In this system, the articles to be sterilized are pretreated with vapor from a solution of hydrogen peroxide and subjected to an electromagnetic field. The plasma is formed from the interaction of the electromagnetic field and the water and hydrogen peroxide vapors. Hydrogen peroxide is ultimately converted to water and oxygen in this process, thus eliminating toxic hydrogen peroxide residuals. The '876 patent purposely adds peroxide to the sterilizing chamber. Another similar patent, U.S. Pat. No. 4,756,882, discusses a system in which the source of the hydrogen peroxide is residue left on instruments.

U.S. Pat. No. 5,244,629, inventors Caputo et al., issued Sep. 19, 1993, describes a process for plasma sterilization including exposing an article in a sterilizing chamber to at least one combination sterilizing cycle. Each combination sterilizing cycle includes a pulsed treatment with gaseous antimicrobial agent, removal of the gaseous antimicrobial agent, and a plasma treatment. The pulsed treatment includes one or more pulse-vacuum cycles, each pulse-vacuum cycle includes the steps of evacuating the sterilizing chamber and exposing the article to the gaseous antimicrobial agent with a predetermined pressure profile during a predetermined time. The gaseous antimicrobial agent is preferably carried in a gas mixture with a nonreactive carrier gas. In one embodiment, the predetermined pressure is pulsed. In another embodiment, it is ramped. After the pulsed treatment, the antimicrobial agent is removed by evacuating the sterilizing chamber. The plasma treatment includes exposing the article to a plasma having essentially uncharged, highly reactive free radicals and atoms.

BIER vessels are known and used to evaluate the resistance performance of biological indicators that are intended for use in monitoring either ethylene oxide or steam sterilization cycles. A description of standards for BIER/EO gas vessels is set out by the Association for the Advancement of Medical Instrumentation (AAMI BEOV—3/82). Similarly, the Association describes performance requirements for the equipment used to determine resistance performance patterns for biological indicators exposed to saturated steam at various temperatures (AAMI BSV—3/81).

However, the performance of a biological indicator intended for use in sterilizers utilizing plasmas has not been adequately monitored by the prior art BIER vessels, and the sterilization conditions in plasma sterilizers are different from those in EO and steam sterilizers. Also, particular strains of microbial spores selected for use as a biological indicator for one type of sterilization process are often not suitable for other sterilization processes or even for differing sterilizing conditions of the same mode of sterilization. The rate at which spores of a biological indicator are inactivated depends on sterilant concentration, so it is important to have a means to determine the concentration of sterilant in a BIER vessel. Further, BIER vessels are, in a limited sense, a type of sterilizer, but BIER vessels must permit significantly greater operator control and are also used to perform "partial" sterilizing cycles in order to obtain survivor curves for biological indicators.

Accordingly, one object of the present invention is to provide a vessel suitable for testing the performance of indicators (biological and/or chemical) when monitoring plasma sterilization processes.

SUMMARY OF THE INVENTION

One aspect of the present invention is a vessel, useful for evaluating the performance of an indicator under sterilization conditions, comprising a chamber in which a sterilizing species is distributed within a predetermined time, a plasma generator adapted to generate a plasma upstream of the chamber, and a monitor associated with the chamber and capable of determining a concentration of selected species in the plasma. The chamber is of a sufficient volume to receive a biological and/or a chemical indictor for testing. The monitor is preferably downstream of the chamber and includes a mass spectrometer, a photometer, or a filter. A preferred embodiment also includes an emission spectrometer upstream of the sterilization chamber.

BRIEF DESCRIPTION OF THE DRAWINGS

FIG. 1 is a schematic illustration of one embodiment of this invention; and

FIG. 2 is similarly a schematic illustration of a second embodiment of the invention, partially broken away.

DETAILED DESCRIPTION OF THE PREFERRED EMBODIMENTS

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. However, ethylene oxide is now known to be a dangerous carcinogen, and a number of new laws protecting worker safety and the environment are precluding further use of ethylene oxide sterilizers in hospital environments. Accordingly, plasma sterilization processes have been developed.

The present invention is a vessel that is useful for evaluating the performance of indicators being subjected to plasma sterilization conditions. For example, the inventive vessel embodiment may be a BIER vessel useful for evaluating the resistance performance of biological indicators and can be used to develop survivor curves of the biological indicators, particularly those involving gas or vapor sterilization processes where the biological indicator is contained in a package.

For example, U.S. patent application Ser. No. 08/111,989, filed Aug. 25, 1993, describes biological indicators comprising a selected number of viable organism spores contained in a package. The organism is *Bacillus circulans*. The package is impenetrable to microorganisms (that is, substantially bacteria impermeable), but has sufficient permeability to let a sterilizing amount of vapor come into contact with the spores during vapor sterilizing processes, such as a plasma sterilization process. The inventive vessel can be used to evaluate the resistance performance of such packaged biological indicators in a sterilizing cycle involving plasma.

Biological indicators using *Bacillus circulans* as the organism are advantageous in gas sterilizing processes since the organism is considered non-pathogenic, is stable enough to provide a relatively long shelf life when packaged, is easy to grow so that sterility tests can be performed using common techniques and materials, and has been found to have a higher resistance and more stable resistant pattern when compared to prior art organisms such as *B. subtilis* and *B. stearothermophilus*. However, it should be understood that BIER vessels of this invention can be used to evaluate the resistance performance of a wide variety of biological indicators, which have different organism spores and may be packaged or unpackaged.

The term "sterilization" connotes a process by which all viable forms of microorganisms are destroyed or removed from an object. Under ideal conditions, microorganisms die according to first order chemical kinetics, it is customary to define sterility in terms of "probability of survivors." The practical goal of a sterilization process is therefore measured as a probability (e g., $10^{-3} 10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the exposure time under identical conditions would double the logarithm of the survival probability, for example $10^{-6}$ would become $10^{-12}$.

The term "plasma" as used herein is defined to include a fully ionized or partially ionized gas. We contemplate use of a "downstream plasma," which is also sometimes referred to as a "secondary plasma," since the downstream or secondary plasma is believed to use uncharged species which act as oxidizing or reducing agents that have been made highly reactive by activation; however, the invention is not limited to this theory, and it may be that atomic (or excited molecular) forms generated in or as a result of the plasma are oxidizing or reducing species. The activation is a result of an applied electric or electromagnetic field, including any accompanying radiation which might be produced. The electromagnetic field can cover a broad frequency range, and can be produced by a magnetron, klystron, or RF coil. For purposes of clarity of presentation and not by way of limitation, the description hereinafter frequently will describe the use of a magnetron as the electromagnetic field source, but the use of all other suitable sources of the electromagnetic field required for plasma production are intended to be included in this invention, including without limitation, magnetrons, klystron tubes, RF coils, and the like.

Generally, a plasma is generated with an initial large component of high energy ions and ultraviolet (UV) emission as a matter of course. As the plasma is transported downstream and out of the plasma generating energy field, the charged particles recombine by collision with container surfaces to uncharged energized free radicals, atoms, and molecules.

The inventive vessel is useful in testing the performance of biological indicators used to monitor the performance of a gas plasma sterilizer where the plasma is generated by any of the various means known to the art, including the plasma sterilizer as described in U.S. Pat. No. 5,244,629 and as described in U.S. Pat. No. 5,184,046, issued Feb. 2, 1993. The former uses a rectangular waveguide. The plasma generator of U.S. Pat. No. 5,184,046 uses a cylindrical waveguide plasma generator.

In addition to the variety of plasma generators useful with the inventive vessels, the plasmas can be made from a variety of gas mixtures, such as are described, for example, by U.S. Pat. No. 5,115,166, issued May 19, 1992. An illustrative gas mixture contains, for example, an inert gas such as argon or helium, and gases such as oxygen and/or hydrogen. Other gases are also known and can be used to produce a plasma sterilizing cycle (e.g. formaldehyde).

Biological indicator survivor curves can be generated by using the inventive vessel as a BIER vessel. Example 4 described hereinafter illustrates an experimental methodology for preparing survivor curves.

In addition to utility in monitoring the efficacy of a plasma sterilization cycle, the inventive vessel optionally is adapted to monitor a fluid sterilizing cycle (in addition to plasma), such as a cycle involving a fluid antimicrobial agent. Chemical indicators are useful in indicating such exposure to a fluid antimicrobial agent (or a component or reaction product of the agent), and Example 5 described hereinafter illustrates this aspect of the invention.

An illustrative group of antimicrobial agents are peracids, which include well known peracid antimicrobial agents such as saturated and unsaturated peralkanoic acids including peralkanoic acids having from 1 to 8 carbon atoms and halogenated derivatives thereof. Examples of suitable peracids include known peracetic acid, halogenated peracetic acids, performic acid, perpropionic acid, halogenated perpropionic acids, perbutanoic acid and its halogen derivatives, perisovaleric acid and its halogen derivatives, percapronic acid and its halogen derivatives, percrotonic acid, monopersuccinic acid, monoperglutaric acid, and perbenzoic acid, for example. The halogenated peracids contain one or more chloro, bromo, iodo, or fluoro groups. The preferred peracids are sufficiently volatile to form an effective sporicidal vapor concentration at temperatures less than 80° C.

If the antimicrobial agent exists in a liquid state at room temperature, it is first vaporized at an elevated temperature preferably not exceeding the operating temperature of the sterilization chamber. This is to keep the temperature(s) high enough and the vapor concentrations low enough to prevent condensation. For considerations of stability, ease of transport, and higher operating pressures, the vaporized antimicrobial agent may be carried in a mixture with a nonreactive carrier gas such as an inert or noble gas. Water vapor may also be mixed with the gaseous antimicrobial agent to enhance its sterilizing action. It has been discovered that with vaporized peracetic acid as the antimicrobial agent, a relative humidity of 20% to 100% further enhances the effectiveness.

Chemical indicators need not respond to all the components necessary for sterilization, but rather can respond to one or more physical or chemical components in the sterilization environment. Since a chemical indicator response may occur in the absence of one or more essential sterilization components, as earlier noted the indicator response is not necessarily an indication of sterility. The chemical indicator only indicates that it has been processed in a sterilizer. Suitable chemical indicators for indicating exposure to peracetic acid and/or to acetic acid vapor, for example, will be hereinafter described.

In addition, the antimicrobial agent may be hydrogen peroxide vapor, such as may be produced by completely evaporating 1% to 10% (wt/wt) hydrogen peroxide solution and preferably from 2% to 8% (wt/wt) hydrogen peroxide solution.

One BIER vessel embodiment of this invention is shown in FIG. 1. The BIER vessel 10 includes a plasma generator 12 and a sterilizing chamber 14. Plasma generator 12 is adapted to generate a plasma that contains a plurality of atomic and/or molecular species, at least one of which has an observable emission of electromagnetic radiation. The emission spectrum from the plasma shows light from one, and typically several or even many plasma species, although the light may not necessarily be directly associated with active sterilization species. Monitoring light from the plasma demonstrates the consistency and reproducibility of the plasma and as a consequence the consistency and reproducibility of the sterilizing environment.

The plasma generator 12 generates plasma upstream of sterilizing chamber 14 and thus the sterilizing cycle is delivered downstream into chamber 14. As already mentioned, we refer to this as the "downstream plasma." Plasma generator 12 may be of the type that includes magnetron 16, waveguide assembly 18, and a plasma chamber 20 into which gas (such as a gas mixture) enters from gas inlet 22. As will be more fully described hereinafter, gas flows in through gas inlet 22, through the plasma generator 12, then through the sterilizing chamber 14, and exits through a vacuum pump.

As already noted, the particular form taken by the plasma generator can vary, and with reference to FIG. 2 another embodiment for plasma generation is shown. Thus, the plasma generator 12' includes magnetron 16', rectangular waveguide assembly 18', and plasma chamber 20'. Gas inlet 22' similarly admits the gas, such as a selected gas mixture, into plasma chamber 20'. Further, plasma generator 12' preferably includes a fiber optic port 24' with which an emission spectrometer 26' is desirably connected for monitoring the plasma being generated. Emission spectrometer 26' is useful for monitoring plasma consistency and reproducibility from one sterilizing cycle to another.

Returning to FIG. 1, the plasma generator 12 embodiment disclosed herein is preferably capable of producing plasma having uncharged, highly reactive species in addition to energetic charged particles (ions and electrons) and UV light. For example, in the plasma generating chamber 20, gas is energized by microwave radiation and forms a plasma having an initial high concentration of ions and ultraviolet emissions. These are preferably not allowed into the sterilization chamber 14, as they tend to be strongly corrosive on the article to be sterilized, or the packaging. The UV emissions are thus localized in the plasma generating chamber and are attenuated, such as by restriction means and/or plasma distribution means. Charged particles entering the chamber can recombine in the gas distribution means, which increases the concentrations of the reactive, electrically neutral species. By the time the plasma enters the sterilizing chamber, the plasma's active downstream products consist essentially of highly reactive uncharged atoms and free radicals and uncharged electronically excited molecules.

Typically, a microwave source will be used to generate the plasma. It is channeled by waveguide 18 to form a highly confined EM field zone. Little of that field can spread to the sterilizing chamber. Thus, production of high energy ions and UV is only possible in the field region of the plasma generating chamber 20 and not outside of it. Also, there is no EM field to cause non-uniformity in the sterilizing chamber.

Plasma generator 12 delivers activated gas into sterilizing chamber 14 through inlet 28. In addition to inlet 28, sterilizing chamber 14 also preferably includes at least one other inlet 30 to deliver the optional additional sterilizing species, here shown as a pair of inlets 30, 32 spaced radially outward with respect to inlet 28.

Sterilizing chamber 14 is typically relatively small. For example, chamber 14 is preferably configured with a circular cross-section and, because small size assists in uniformity of sterilizing conditions brought to steady state quickly, we prefer diameters on the order of about one foot or smaller, and cylindrical heights of about eight inches or smaller.

Sterilizing chamber 14, in a limited sense, is a sterilizer of sorts; however, BIER vessels must perform so that the conditions to which the BIs are subjected are uniform. In addition to uniformity, another important aspect of the inventive BIER vessel is that the BIs being tested are exposed to sterilization conditions that reach a steady state in as short a time as practically possible. For example, in steam BIER vessels, the temperature must rise to the set point within ten seconds of the start of the test, while at the end of the test the steam must be vented away within five seconds. The required rise time in EtO vessels are somewhat slower.

Chamber 14 is of sufficient construction to distribute sterilizing species uniformly throughout the useful volume of the sterilizing chamber for the duration of the cycle. In constructing chamber 14, glass, quartz, stainless steel, and aluminum are preferred construction materials. For BIER vessel embodiment 10, such uniform distribution is preferably achieved, in addition to the relatively small size of chamber 14, by the inclusion of at least one, preferably a plurality, of gas distributors 34, 36 within chamber 14. Gas distributors 34, 36 are preferably formed of quartz, since quartz is inert and can withstand elevated temperatures. However, the distributors can also be glass, or can be made of metal coated with a polymer such as Teflon. The polymer should be resistant to, that is not degraded by, the plasma. The distributors 34, 36 preferably serve as baffles and have uniformly distributed holes. Distributor 34 thus provides many entrance points through which the reactive species may flow into the sterilization chamber, and distributor 36 provides many points through which the reactive species may be exhausted from the chamber. Thus, the concentration of the reactive species is caused to be uniform across the sterilization chamber. When an antimicrobial agent is used, the distributors aid in insuring that the vaporized agent is dispersed uniformly throughout the chamber. Distributor 34 is mounted in chamber 14 adjacent to inlets 28, 30, and 32 and distributor 36 is mounted in chamber 14 adjacent to outlets 40, 42, as will be hereinafter described.

A specimen support, or mount, 44 protrudes into chamber 14. Specimen support 44 is used to hold the indicator (biological and/or chemical) being tested in chamber 14 when the plasma sterilizing cycle or the additional sterilizing cycle is performed. The specimen is placed on support 44, which is preferably equipped with a temperature monitor (not illustrated) in the vicinity of the samples and which optionally may be fitted with a temperature controller for controlling the temperature of the samples. Walls 46 of chamber 14 preferably have a means to maintain the wall temperature within relatively narrow bounds. For example, walls 46 can be in contact with a water jacket (not illustrated) so that water being pumped through the jacket will maintain the wall temperatures as desired. This improves uniformity and reproducibility.

Walls 46 of chamber 14 are preferably formed of or lined with quartz, glass such as Pyrex, or a ceramic. A door 48 is secured in a sealed relationship with the sterilizing chamber 14. Support 44 may be attached to door 48 so that when door 48 is removed samples can be mounted or removed.

The chamber 14 and door 48 can be made of any material having the strength required to withstand the external atmospheric pressure when the chamber is evacuated. Stainless steel or aluminum plates for the door are preferred. The internal surface material of the chamber affects the number of killing species available in the chamber. As already mentioned, quartz, glass, and ceramics are suitable. Another suitable material is an inert polymer such as polytetrafluoroethylene (Teflon). An alternate material is pure (98%) aluminum which can be applied either as a liner or as a flame-sprayed coating on all internal walls of the stainless steel chamber. Another alternate material is nickel.

During the plasma sterilization cycle for BIER vessel 10, the plasma is continuously flowed through sterilization chamber 14. Plasma is flowed by means, for example, of a vacuum pump (not illustrated). We prefer a pump capable of maintaining pressure in chamber 14 during a plasma sterilizing cycle of between about 10 mTorr to about 100 Torr with a preferred flow rate of about 1 to 2 standard L/min or lower. An illustrative suitable pump is a rotary vane pump with a Roots blower. Chamber 14 is in fluid communication with the pump at outlet 40 and a throttle valve 55 is useful to control chamber pressure independently of gas flow rates.

Chamber 14 has another outlet 42 whereby a monitor 52 monitors (or determines) the concentration of selected species in a plasma sterilizing cycle downstream of chamber 14. Monitors attached to the sterilization chamber can monitor electromagnetic radiation emitted by long-lived (metastable) excited atoms and molecules, which are transported into the chamber. The emissions are distinct from the emission seen in the plasma generating chamber, which generally arise from short lived excited states.

The monitor 52 may include, for example, a mass spectrometer, a photometer, or a filter. The monitor 52 illustrated is a mass spectrometer, which is connected to the interior of a chamber 54, for example, to permit monitoring of the various combination of gases employed in the plasma. Chamber 54 preferably can be evacuated to a high vacuum (approximately $10^{-6}$ Torr) by means such as a turbo molecular vacuum pump 56. A vacuum gate valve 58 admits a small quantity of sterilizing species in chamber 14 through, for example, a small orifice such as an orifice having a diameter of about 25μ to about 100μ. As is well known, gases entering the mass spectrometer are bombarded by electrons. As a result, the chemicals become electrically charged. They may also break into charged fragments. The mass spectrometer measures the mass and the abundance of these fragments. Thus, the mass spectrometer may be used to monitor the composition (partial pressures) of stable gases in the chamber during the plasma process, as well as the optional antimicrobial cycle.

Since the plasma contains a plurality of atomic and/or molecular species, which each have an observable emission of electromagnetic radiation, the emission spectrometer (shown in FIG. 1 as 26 and in FIG. 2 as 26') may be used to monitor the spectral lines of the glow discharge during the plasma phase of the process. As the excited electrons return to lower energy states, eventually reaching their normal states (also called unexcited states or ground states), they emit radiation. Some of this radiation can be detected as light. Each electronic transition is associated with light of a certain wavelength. By determining the wavelengths of the light emitted by the plasma, it is possible to determine some of the chemical species present in the plasma. Also, determining how the intensities of the spectral lines in the plasma change over time gives some indication of how the plasma itself is changing over the same period of time.

The intensities of the strongest emission lines, particularly those from oxygen and hydrogen, are measured and can be used to diagnose the characteristics of the plasma and then to make any adjustments to the relative proportion of the gaseous components that are required or desired to maintain the plasma in a desired condition. For example, one can monitor the hydrogen lines at about 657.1 nm and 486.1 nm wave lengths, oxygen lines at about 777.2 nm and 844.6 nm, the hydroxyl line at 306.4 nm, and argon lines at 811.5 nm and 763.5 nm.

Since these emission peaks are very strong relative to the intensity of the surrounding portion of the spectra, and are very narrow in band width, the spectrometer need have only a resolution capability of about 0.5 nm, which is well within the resolving powers of commercially available instruments. Known methods of plasma diagnostics and control are usefully employed in order to provide a plasma with uniform and repeatable sterilizing characteristics in sterilization chamber 14.

In addition to or in lieu of a mass spectrometer and/or an emission spectrometer, monitor 40 can include a photometer which is useful in monitoring amounts of species in a sterilizing cycle such as by gas phase titration. That is, gas phase titration can be used as a method for calibrating the gas flow and determining the concentration of selected gases, such as is known to the art. For example, U.S. Pat. No. 4,314,344, issued Feb. 2, 1982, Johns et al., describes use of a photometer to calibrate gas flow and to determine concentration of gaseous species therein. Other techniques and equipment useful in performing the monitoring function includes resonance fluorescence techniques.

It will be understood, and as well known to the art, that additional factors may affect the sterilization of biological indicators, including temperature, pressure, and relative humidity. Therefore, any of the conventional temperature, pressure, or humidity monitoring means may be used. Therefore, any of the conventional pressure and temperature (also relative humidity) monitoring means may be used in conjunction with the BIER vessel embodiment of this invention. For example, monitoring means for other factors can include a timer preferably accurate to ±1 second, a temperature controller and/or monitor preferably accurate to ±1° C., and vacuum gauges for monitoring the pressures of chambers 14 and 54, preferably accurate to ±0.05 Torr and ±1×10$^{-7}$ Torr for the respective chambers.

The operation of embodiments in accordance with this invention will now be illustrated by several examples, which are intended to be illustrative and not limiting.

With reference to the FIG. 1 apparatus, a first BIER system had a flat bottom piece made of aluminum and lined with quartz; an aluminum cylinder about 12 inches in diameter and 4 inches high sat on the base (also quartz lined); a pyrex cylinder about 12 inches in diameter and 4 inches high on top of the aluminum cylinder; and a flat quartz-lined aluminum top piece on top of the Pyrex cylinder. A plasma generator was mounted on top of the top plate and gases were exhausted through a port in the bottom plate. Inside the chamber were two diffusers, an inlet diffuser and an exhaust baffle. These were very similar in construction. Both were shallow flat pans of quartz with an array of holes in the bottom. The inlet diffuser was mounted so the flat surface with the holes was about one inch below the top piece. The exhaust baffle was mounted so the flat surface with the holes was about one inch above the bottom piece. The chamber also housed a sample stage made of perforated aluminum. The stage was about 9¼ inches by 1½ inches and was mounted about 1 inch above the exhaust baffle.

For this first embodiment the plasma was generated in a cylindrical aluminum waveguide about 4¼ inches in OD and 5¾ inches high. A 540 W magnetron was mounted on top of the waveguide with the antenna on the cylindrical axis of the waveguide. Gases flowed through a quartz bulb into the waveguide. The bulb was about 95 mm OD and filled most of the waveguide between the magnetron antenna and the bottom of the waveguide. Gases were introduced into the top of the bulb through a side arm and passed from the bulb into the sterilizing chamber through a tube in the center of the bottom of the bulb. The magnetron was operated at a power of 270 W.

The mass spectrometer of the first embodiment was a commercial unit (Balzers High Vacuum Products) with a mass range of 1–200 amu. The mass spectrometer was mounted on the bottom plate of the chamber. Between the chamber and the mass spectrometer was a gate valve and a pressure-reducing orifice consisting of a piece of molybdenum foil 0.002 inches in thickness with a 50 μm hole etched in the center. The ion source of the mass spectrometer was positioned so the inlet tube pointed at the hole in the molybdenum foil. The end of the inlet tube was about 1 cm from the hole in the foil. The mass spectrometer was pumped by a turbomolecular pump (170 l/sec) backed by a rotary vane pump (1.2 cfm).

The top of the system was held at 20° C. by means of cooling water which circulated through a heat exchanger mounted to the top plate. The bottom of the system was warmed by a heater attached to the mass spectrometer manifold.

The emission spectrophotometer 26 of the first embodiment included a 1 m quartz fiber optic cable to conduct light from the plasma chamber to the monochromator. This cable was mounted in the side of the plasma waveguide through a hole 24 about 2 inches from the top of the waveguide. The fiber optic cable pointed toward the centerline of the waveguide. The monochromator (Thermo Jarrell-Ash) was equipped with a 150 line/mm diffraction grating and a 300 line/mm diffraction grating blazed to provide maximum signals at 450 and 300 nm, respectively. The monochromator was equipped with a 25 μm entrance slit and a 1024 element unintensified photodiode array detector (EG&G Princeton Applied Research). The mass spectrometer and emission spectrophotometer were connected to a computer through electronic interface circuits provided by the manufacturers, and data was collected using software provided by the manufacturers.

The experiments described in Example 1 investigated the emission spectrum of the light emitted from the glow discharge used in the plasma cycle of a sterilization process. The experiments described in Example 2 investigated the mass spectrum of the gases found in the chamber during the plasma cycle.

A second embodiment of the vessel was also characterized. In this embodiment, a plasma generator using a rectangular waveguide (FIG. 2) was used instead of the cylindrical waveguide shown in FIG. 1. Experiments in which the emission spectrum of the plasma and the mass spectrum of the gases in the sterilization chamber are characterized are described in Example 3.

For the second embodiment, the waveguide was equipped with a magnetron operated at 540 W (full power). The tube in which the plasma was generated was made of quartz with an outer diameter of 18 mm. A quartz gas flow restrictor with inside diameter 4.8 mm was placed at the base of the base of the plasma generating tube. The sterilization chamber, emission spectrophotometer, and mass spectrometer were the same as those described in the first embodiment, with minor changes to accommodate mounting the plasma generator. Example 3 sets out experiments in which the characteristics of the emission spectrum of the plasma and the mass spectrum of the gases in the sterilization chamber during the plasma cycle were evaluated.

EXAMPLE 1

(Emission Spectrum Characterizations)

Plasma was formed using a gas flow of 1.85 slm, a gas composition of approximately 4% hydrogen, 5% oxygen, and 91% argon, and a magnetron power of 270 W. The pressure in the sterilizing chamber was maintained at 1.0 Torr. Several emission spectra were obtained. The most prominent spectral lines were identified from their wavelengths. All the lines were associated with hydrogen, oxygen, argon, or hydroxyl radicals, which are formed by reactions between oxygen an hydrogen. The most prominent lines from hydrogen were observed at 486.1 nm and 656.3 nm; the most prominent oxygen lines were observed at 777.2 and 844.6 nm; and hydroxyls produced a major line at 306.4 nm and a smaller line at 281.1 nm. The other major lines observed were associated with argon.

To determine how emission line intensities changed over time, spectra were recorded as soon as the plasma was turned on and at approximately one minute intervals for the following twenty minutes. This experiment was repeated six times. The intensities of each line were normalized to the time zero intensity.

These plots showed good run to run reproducibility for the intense lines. Most of the line intensities increased slightly with time (about 0 to 20%). The OH lines increased about 50% after 19 minutes, and the O and H lines remained fairly constant.

EXAMPLE 2

(Mass Spectrum Characterization)

Mass spectra in the range of 1–50 amu were taken with the BIER vessel operating with the same gas flows described in Example 1, but with the magnetron turned off. All the major peaks were found to be associated with argon (40, 38, 36, 20, and 13.33 amu), oxygen (32 and 16 amu), hydrogen (1 and 2 amu), and water (18, 17, 16, and 1 amu). The peaks were quite symmetric with the exception of the Ar 40 amu peak, which was so high it caused detector saturation and associated artifacts.

Other spectra were taken with the magnetrons energized. When the magnetron is energized, the molecular oxygen peak (32 amu) and the molecular hydrogen peak (2 amu) drop; the water peak at 17 and 18 amu increase; and the argon peaks remain constant.

The mass spectrometer was configured to monitor the intensity of the most prominent spectral lines over a 50 minute period. Gas was allowed to flow through the system and data acquisition started. The magnetron was off for the first 10 minutes. The magnetron was then turned on for 15 minutes and was then turned off for one minute. At the end of this period, the gas flow was turned off and the chamber was evacuated and "background" spectra were acquired.

The resulting data was consistent with the hypothesis that the plasma causes oxygen and hydrogen to react and form water. The data also shows that this reaction, as well as the gas composition in the sterilization chamber, is consistent from experiment to experiment. The levels did not vary within the experiment (i.e. a certain set of constant levels was seen with the plasma off, and a second set, also constant, was seen with the plasma on).

EXAMPLE 3

(Emission Spectra)

The rectangular waveguide and its associated light collection apparatus have provided spectra which are very similar to those obtained earlier with the first embodiment. These spectra are quite reproducible on a cycle to cycle and day to day basis. The oxygen lines are much more pronounced in these spectra than in those earlier. The intensities of most lines in these spectra increased significantly during the first two minutes of plasma, after which they reached a plateau.

The second embodiment system was run such that the plasma was turned on for 10 minutes, turned off for 20 minutes, turned on for another 10 minutes, turned off for another 20 minutes, and so forth, for a total of six on/off cycles. The gas flows were the same as in Examples 1 and 2. Emission spectra were accumulated every minute during the periods in which the plasma was on. The experiment was repeated three times on three different days. The intensities of the five lines associated with oxygen and hydrogen and the twelve most intense argon peaks (based on the baseline data) were determined for each of the spectra collected.

In all but two cases, the intensities of the spectral lines were rather low when the plasma was turned on (the 0, 30, 60, 90, 120, and 150 minute time points in each figure). The intensity increased rapidly and reached a plateau within two minutes. The O lines at 777.2 and 844.6 nm approached steady state levels more quickly than the other lines.

The means and the sample standard deviation for the intensity readings made two minutes or more after the plasma was turned on was computed for each spectral line. The maximum and minimum in each set of readings were also determined. On the average, the sample standard deviation was 3.9% of the mean intensity. This figure ranged from a low of 0.6% for the 617.2 Ar line to 5.5% for the 794.8 nm Ar line. These data also indicate that the plasma composition is reproducible from experiment to experiment and from day to day.

The mass spectroscopy data are in agreement with the data collected in the earlier studies with the first embodiment. When the plasma is turned on, the levels of peaks associated with molecular oxygen and hydrogen decreased, and those associated with water increased. Argon peaks remained fairly constant. As was seen in the emission spectra, it takes the oxygen peaks two or three minutes to reach steady state levels once the plasma is turned on. In contrast, the water peak increases throughout a 10 minute plasma cycle. Within the limits of the reliability of the mass spectrometer, the behavior of the mass peaks is reproducible from cycle to cycle and from day to day.

EXAMPLE 4

Since particular strains of microbial spores selected for use as a biological indicator for one type of sterilization process are often not suitable for other sterilization processes or even for differing sterilizing conditions of the same mode of sterilization, preferred biological indicators for use with the sterilization processes practiced in BIER vessels of the invention will now be described.

Packages for biological indicators may be obtained from Baxter Laboratories as "Plastipeel Pouches." These pouches have an upper sheet of a gas permeable fabric of bound polyethylene fibers ("Tyvek"), which is already sealed on three edges and where the user seals the fourth edge, after insertion of the carrier, to a lower sheet of impermeable clear polyester film ("Mylar"). Filter paper disks (¼ inch diameter Schleicher & Schuell 740E) may be used as the carriers. Each disk may be inoculated with $10^6$ spores of viable organism. For comparative survivor curve experiments, each pouch may contain two paper carriers, one with *Bacillus circulans* spores and the other with *Bacillus subtilis*. In comparing survivor curves and performing fraction negative analyses for spores of *Bacillus subtilis* and others with *Bacillus circulans*, heat seals may be used to create separate compartments.

Exposure intervals for exposure to the sterilizing gas will be chosen. The biological indicators may be exposed to only a peracetic acid cycle, only a plasma cycle, or both cycles for the selected exposures. The amount of peracetic acid vapor for a cycle may be approximately 2 mg/L, and the vapor may be obtained by evaporating a peracetic acid solution. Thus, in addition to what is believed to be the primary gaseous oxidizing species of peracetic acid, the vapor also may include hydrogen peroxide and acetic acid (and water). The feed gas for the plasma generated gaseous mixture may be argon, oxygen, and hydrogen, which may be prepared with about 91.4% argon, 3.8% hydrogen, and 4.7% oxygen and for a cycle flowed at a volume of about 5.5 standard L/min. The combined treatment (both sterilants) may use peracetic acid vapor exposure for a time interval double that (and preceding) treatment with the plasma generated gas mixture. For example, the three minute exposure time may involve exposing the carriers to peracetic acid vapor for two minutes and then subjecting them to the plasma process for one minute.

After exposing the biological indicators to the sterilizing gas treatment (the wall temperature may be maintained at about 95° F.) the indicators will be removed and tested for sterility.

Each pouch may be cut open and each carrier aseptically transferred to labelled, individual grind tubes. Each tube may be vortexed until the carriers are macerated. Each macerated carrier may be serially diluted using standard plate count techniques. The number of surviving spores (if any) may be determined under spore growth conditions.

Survivor curves with the number of surviving spores may be determined as a function of exposing step time. D-values for the separate components may be calculated using linear regression analysis. D-values (decimal reduction) are the time required at a given set of exposure conditions to reduce a specific population by 90%, and are the negative reciprocal of the slope of the line fitted to the graph of the logarithm of the number of survivors versus time.

EXAMPLE 5

Sterilization processes preferably have chemical indicators adapted to indicate whether or not exposure to the sterilization process has occurred. Thus, the preparation of suitable chemical indicators for use in conjunction with BIER vessels of the invention will now be described.

Chemical indicators useful for indicating exposure to an antimicrobial fluid (in this case, peracetic acid, whose component or reaction product, acetic acid, causes a color change) may be prepared by admixing the following components:

| gm/L | |
|---|---|
| 0.4 | dye (Bromophenol Blue, 0.1 g in 14.9 ml 0.01N NaOH plus 235.1 ml water) |
| 3.0 | pH adjusting agent (0.01N acetic acid, sufficient to adjust to pH 6.5) |
| 4.0 | thickener/binder (2.5 gm/L silica and 1.5 gm/L bentonite) |

The just described dye composition may be applied to substrate by placing a coil of chromatography paper, such as Whatman 3 MMCHR, in a beaker of the dye composition and leaving it in the beaker for a few minutes. The paper may then be removed, drained, dried, and cut into pieces. The indicators may then be individually sealed in Tyvek/Mylar pouches (commercially available as Tower Plasti-Peel pouches) and the package edges sealed by heating.

The chemical indicator pouches may be exposed to a complete sterilization (for example, six peracetic acid cycles each consisting of a 20 minute exposure to peracetic acid vapor followed by 10 minute exposure to plasma) or partial sterilization processes. The peracetic acid formulation may use a solution of 10% PAA, 11% acetic acid, 2% $H_2O_2$, less than 1% nonvolatile stabilizer and sulfuric acid, and the balance water.

Exposure to the complete sterilization process will cause the indicators to turn from dark blue to light yellow (which represents not only a color change but also a contrast change).

EXAMPLE 6

The inventive embodiment BIER unit used the rectangular waveguide shown in FIG. 2. Plasma was formed using a gas flow of 2 slm. The gas composition was approximately 2.8% $O_2$, 2.2% $H_2$, and the balance argon. Peracetic acid vapor was not used. The pressure in the sterilizing chamber was maintained at about 0.73 Torr.

The indicators used were *B. circulans* inoculated onto discs of filter paper and packaged in Tyvek/Mylar sterilization pouches (i.e. the "Plastipeel" pouches described above). One pouch held three inoculated discs. Three discs were run in each test. After processing in the vessel, survivors were determined by enumeration techniques previously described above.

Tests were performed using 2, 4, 6, 8, 10, and 12 minute exposures. Two sets of tests were run on different days. The results are summarized in Table I (below).

TABLE I

| Time (min) | Test 1 Average | Test 1 STD | Test 2 Average | Test 2 STD |
|---|---|---|---|---|
| 0 | 6.49 | 0.02 | 6.38 | 0.06 |
| 2 | 6.52 | 0.03 | 6.29 | 0.02 |
| 4 | 6.34 | 0.04 | 6.05 | 0.10 |
| 6 | 5.27 | 0.46 | 4.69 | 0.63 |
| 8 | 3.08 | 0.61 | 2.43 | 0.74 |
| 10 | 1.48 | 0.62 | 1.19 | 0.33 |
| 12 | 0.92 | 0.68 | 0.66 | 0.46 |

("Average" refers to the average of the logarithms of the numbers of survivors. "STD" refers to the sample standard deviation of the logarithms of the numbers of survivors.)

These data indicate the reproducibility of the plasma portion of the sterilization process. They also show that the sterilization process follows first order kinetics since after a lag of about 4 minutes, the number of survivors decreases exponentially. Using the 4, 6, 8, 10, and 12 minute time points, it can be calculated that the D-value (time needed to kill 90% of the remaining survivors) in test 1 was 1.37 minutes. The D-value in test 2 was 1.40 minutes.

It is to be understood that while the invention has been described above in conjunction with preferred specific embodiments, the description and examples are intended to illustrate and not limit the scope of the invention, which is defined by the scope of the appended claims.

It is claimed:

1. A vessel, useful for evaluating the performance of an indicator under sterilization conditions, comprising:

a chamber defining a volume, the volume adapted to receive a biological and/or chemical indicator, the chamber of sufficient construction uniformly to distribute a cycle of a sterilizing species in the volume within a predetermined time;

a plasma generator adapted to generate a plasma upstream of the chamber and in communication with the chamber, the plasma containing a plurality of atomic and/or molecular species;

pumping means for continuously flowing plasma through the chamber during a plasma sterilizing cycle while maintaining a reduced pressure in the chamber; and a monitor operatively associated with the vessel and capable of determining a concentration of selected species in the plasma when a plasma sterilizing cycle constituted entirely or in part by the plasma is flowing through the volume.

2. The vessel as in claim 1 wherein the monitor is downstream of the chamber and includes a mass spectrometer, a photometer, or a filter.

3. The vessel as in claim 1 further comprising an emission spectrometer operatively associated with the chamber or the plasma generator and of a construction sufficient to determine plasma consistency in the plasma generator.

4. The vessel as in claim 1 further comprising:

a source of antimicrobial fluid in fluid communication with the chamber.

5. The vessel as in claim 1 further comprising:

a source of a plasma forming gas mixture in fluid communication with the plasma generator.

6. The vessel as in claim 1 wherein the cycle of sterilizing species has a plurality of determinable characteristics that affect sterilization, and further comprises:

means for monitoring one or more of the characteristics affecting sterilization of the biological indicator being evaluated.

7. The vessel as in claim 6 wherein the vessel is adapted to evaluate resistance performance of biological indicators, and the characteristics affecting sterilization of the biological indicator include temperature and pressure within the volume.

8. A system for testing sterilization processes, comprising:

a chamber defining a volume, the chamber of sufficient construction uniformly to distribute a cycle of a sterilizing species in the volume within a predetermined time;

a plasma generator adapted to generate a plasma upstream of the chamber and in communication with the chamber, the plasma containing a plurality of atomic and/or molecular species;

a monitor operatively associated with the vessel and capable of determining a concentration of selected species in the plasma when a sterilizing cycle constituted entirely or in part by the plasma is flowing through the volume; and a biological and/or chemical indicator adapted to be disposed within the chamber volume.

9. The system as in claim 8 wherein the indicator is a biological indicator using *Bacillus circulans* spores.

10. The system as in claim 8 wherein the indicator is a chemical indicator adapted to indicate sterilization cycle exposure when the sterilization cycles includes use of peracetic acid.

11. A BIER vessel, useful for evaluating the performance of an indicator under sterilization conditions including use of a plasma, comprising:

a chamber defining a volume;

a plasma generator adapted to generate a plasma upstream of the chamber and being in communication with the chamber, the plasma including an oxygen species and a hydrogen species;

distribution means for uniformly distributing plasma entering the chamber within the volume within a predetermined time;

pumping means for continuously flowing plasma through the chamber during a plasma sterilizing cycle while maintaining a reduced pressure in the chamber; and means for monitoring the plasma within the chamber or the plasma generator, the monitoring means including an emission spectrometer and a mass spectrometer.

12. The BIER vessel as in claim 11 wherein the emission spectrometer is adapted to determine plasma consistency via spectra of at least the oxygen species and the hydrogen species.

13. The BIER vessel as in claim 11 wherein the monitoring means is adapted to monitor electromagnetic radiation emitted by short-lived excited states of plasma species, long-lived excited states of plasma species or both.

14. The BIER vessel as in claim 11 further comprising a source of peracetic acid in fluid communication with the chamber.

15. A BIER vessel, comprising:

a chamber defining an evacuatable volume in which an indicator can be disposed;

a plasma generator in communication and upstream with respect to the chamber, the plasma generator capable of generating a plasma from at least one gaseous species upstream of the chamber;

at least one baffle, the at least one baffle being interposed between the plasma generator and an indicator when disposed in the chamber volume, the at least one baffle being of a construction sufficient to distribute plasma entering the chamber within the volume adjacent to the indicator; and, a mass spectrometer operably associated with the vessel to determine a concentration of a selected species in the plasma when the volume is evacuated and the plasma is flowed into the volume.

16. The BIER vessel as in claim 15 wherein the mass spectrometer is downstream of the chamber.

17. The BIER vessel as in claim 15 or 16 further comprising a source of antimicrobial fluid in fluid communication with the chamber.

18. The BIER vessel as in claim 17 wherein the antimicrobial fluid is an oxidizing fluid.

19. The BIER vessel as in claim 18 wherein the oxidizing fluid includes peracetic acid.

20. The BIER vessel as in claim 15 further comprising an emission spectrometer operably associated with the chamber or the plasma generator to determine plasma consistency in or flowed from the plasma generator.

* * * * *